(12) United States Patent  
Lacombe (10) Patent No.: US 8,843,324 B2  
(45) Date of Patent: Sep. 23, 2014

(54) DOUBLE DERIVATIVE NIR PROCESS CONTROL

(75) Inventor: Yves Lacombe, Calgary (CA)

(73) Assignee: Nova Chemicals (International) S.A., Fribourg (CH)

( * ) Notice: Subject to any disclaimer, the term of this patent is extended or adjusted under 35 U.S.C. 154(b) by 767 days.

(21) Appl. No.: 12/931,520

(22) Filed: Feb. 3, 2011

(65) Prior Publication Data

US 2012/0203472 A1    Aug. 9, 2012

(51) Int. Cl.
*G01N 21/27* (2006.01)
*G01N 21/35* (2014.01)
*G01N 21/85* (2006.01)

(52) U.S. Cl.
CPC .......... *G01N 21/359* (2013.01); *G01N 21/3563* (2013.01); *G01N 21/3577* (2013.01); *G01N 21/85* (2013.01); *G01N 21/274* (2013.01)
USPC ............................................. 702/30; 526/59

(58) Field of Classification Search
CPC .. C08F 10/00; B01J 19/0006; G01N 21/3563; G01N 21/274
USPC ................................................. 702/30; 526/59
See application file for complete search history.

(56) References Cited

U.S. PATENT DOCUMENTS

| | | | | |
|---|---|---|---|---|
| 4,163,831 | A | * | 8/1979 | Gessell .......................... 526/153 |
| 5,151,474 | A | | 9/1992 | Lange et al. |
| 5,155,184 | A | * | 10/1992 | Laurent et al. .................. 526/59 |
| 6,072,576 | A | | 6/2000 | McDonald et al. |
| 6,820,013 | B1 | | 11/2004 | Frickel et al. |
| 6,864,331 | B1 | * | 3/2005 | Reimers et al. .................. 526/59 |
| 2012/0041158 | A1 | * | 2/2012 | Chauvel et al. .................. 526/60 |

OTHER PUBLICATIONS

Franke, "Inverse Least Squares and Classical Least Squares Methods for Quantitative Vibrational Specvtroscopy", Aug. 15, 2006, Handbook of Vibrational Spectroscopy, pp. 2276-2292.*
Yalvac et al, real-time analysis of light alkenes at elevated temperatures and pressures by fiber-optic NIR spectroscopy, Applied Spectroscopy,1997, 1565-1672, vol. 51, No. 10.
Vela Esrada, NIR process monitoring, IP.com publication identifier : IPCOM000134539D, Mar. 9, 2006.

* cited by examiner

*Primary Examiner* — Jonathan C Teixeira Moffat
*Assistant Examiner* — Regis Betsch
(74) *Attorney, Agent, or Firm* — Kenneth H Johnson (57) ABSTRACT

The present invention provides a method to calibrate a NIR analyzer to measure monomer concentrations at one or more locations in a reactor system. The regression coefficients for the NIR analyzer are transferable between reactors using the same process (solution polymerization to solution polymerization) and may be used to control the reaction, or calibrate flow meters on line.

21 Claims, 3 Drawing Sheets

DOUBLE DERIVATIVE NIR PROCESS CONTROL

FIELD OF THE INVENTION

The present invention relates to process for the control of chemical reactions in solution using near infrared spectroscopy (NIR) without the use of a library of spectra. More particularly the present invention relates to NIR process control for chemical reactions where it is not possible or extremely difficult to collect samples, which can be analyzed using off-line analytical method to produce a calibration model for NIR spectroscopy. This is particularly the case in hot high pressure reactions run in a flammable solvent. In the process a monomer concentration is calculated to indirectly indicate conversion and a derivative (i.e. not change the measured variable) variable control mechanism is used (catalyst concentration) to control the reaction. The present invention also provides an online method to monitor or recalibrate monomer flow meter. The measured monomer concentration is compared to a calculated monomer concentration based on feed rates.

BACKGROUND OF THE INVENTION

Spectroscopy for a quantitative analysis of single component possibly in a solvent is based on simple linear regression using Beers' Law. This may be done by generating a calibration curve correlating the absorbance of the component at a specific wavelength with different concentrations of component in the solution. However, this approach does not work with multiple components, particularly if they have overlapping adsorption bands as seen in the Near Infrared Spectral region.

K. Norris of the Department of Agriculture of the United States of America demonstrated in 1968 the possibility of quantitative analysis using NIR spectra for complex mixtures. The technique was based on a multiple linear regression for NIR spectra (NIR-MLR). For example, the protein content of wheat flour ($C_p$) could be expressed as:

$$C_p = K_0 + K_1 L(\lambda_1) + K_2 L(\lambda_2) + K_3 L(\lambda_3) +$$

where $L(\lambda_n)$ represents the absorbance (or its derivative) at wavelength n. When an NIR spectra is taken the values for $L(\lambda_n)$ are determined from the spectra. The wavelengths are selected to give a good regression fit to the calculation (e.g. minimize overlap and interference within the spectra). The regression coefficients $K_1$ etc. are determined by a regression based on an analysis of calibration samples for known values. The model is then validated using different known samples from the calibration samples (validated regression coefficients).

The application of spectroscopy to process control has been known for a number of years. With the advent of high speed computers (microprocessors) spectra may be compared to a library of spectra for various products to determine how the process needs to be controlled/changed to produce a required product. This is not a regression approach but rather a direct comparison—closest fit approach to a known spectrum.

The analysis of light alkenes at high temperature and pressure has also been described by E. D. Yalvac et al.—Yalvac, E. D.; Seasholtz, M. B.; Beach, M. A.; Crouch, S. R.; Real-time analysis of light alkenes at elevated temperatures and pressures by fiber-optic near-infrared spectroscopy—Applied Spectroscopy, (1997), 51(10), 1565-1572, CODEN: APSPA4 ISSN:0003-7028, CAN 127:365507, AN 1997:694589, CAPLUS. In this publication, the real time analysis of light alkene mixtures (ethylene and 1-octene in Isopar E solvent) is discussed. The procedure involves generating a set of calibration spectra for which the composition is determined using a reference method. The experimental design includes a range of concentration, pressure and temperature for the application of interest. The calibration model is then utilized to predict new sample composition. The model predicts composition of mixture for which it was calibrated (i.e. only mixture of ethylene, 1-octene and isopar E). It does not mention the use of the model to measure ethylene and or 1-octene for mixture which include additional chemical component (polymer in a polymerization process).

IP.com publication identifier 'IPCOM000134539D' "NIR Process Monitoring" by Vela Estrada broadly discloses that NIR may be used to monitor chemical processes. The disclosure is quite broad but seems to be limited to direct measurement and control of a variable. For example to control catalyst one directly measures catalyst input or concentration in the reactor and makes appropriate modification to the catalyst flow rate. The reference does not seem to suggest measuring monomer concentration to control the flow of catalyst. Further the disclosure makes no reference to validating flow control systems on line.

U.S. Pat. No. 5,151,474 issued Sep. 29, 1992 to Lang et al. assigned to The Dow Chemical Company discloses the use of Fourier Transform Infrared Spectroscopy (FTIR) to control the manufacture of a polyolefin. The patent teaches the use of the infrared range of light rather than the near infrared. Adsorption measurements at 2120, 1909 and 1829 wavenumbers indicate the background signal and the concentration of ethylene and octene respectively. Based on these measurements the residual monomer content in the recycle stream is determined and the flow of monomers into the recycle stream is controlled to bring the feed stream to the set point for the process control. This is direct control measurement. The monomer concentration is measured and controlled. The patent does not suggest a regression analysis of the sample or the control nor the control by a different parameter.

U.S. Pat. No. 6,072,576 issued Jun. 6, 2000 to McDonald et al. assigned to Exxon Chemical Patents Inc., teaches a process to use on line NIR to control a halobutyl rubber reaction. In the process the instrumentation assembly 500 is mounted at the output of various stages of the reaction (Col. 3 lines 45-60). A number of sample spectra are generated and corrected for baseline error (eigenspectra) and error due to ex-sample chemical compounds present during the measurement process. For each eigenspectra a number of known properties or compositions of the polymer are determined. Then the components of the spectra relating to the property are given ratings or scores (dependent variables). The scores together with other data (viscosity and temperature) independent variables are used as constants in a process control algorithm. The process spectra are analyzed in similar manner to determine the dependent and independent variables which are compared to the process control algorithm. Then changes are made in the operation of the process to maintain the product at the desired specification. The present invention has eliminated the use of additional independent variables such as temperature and viscosity. The present invention does not require physical sample to be taken and analyzed to provide a reference property.

U.S. Pat. No. 6,864,331 issued Mar. 8, 2005, from an application filed Dec. 9, 2003, to Reimers at al. assigned to Fina Technology, Inc., teaches the use of NIR to control a process. Samples of product made in the reactor are analyzed for the desired property (e.g. styrene, polystyrene, diluents, mineral oil, rubber and rubber particle size—Col. 5 lines 60-65). In the present invention the calibration spectra are obtained without polymerization and without taking physical sample, while Reimers based his calibration curves on samples which are polymerized or partially polymerized (i.e. a direct measurement). The examples of Reimers suggest that for some samples a math pretreatment is applied to the spectra before regression (Col. 6 line 9 and 10) but for particle size the math pre treatment must not be used as it would dampen or negate the signal. The math pretreatment is a standard normal variant and a second derivative may be used. Reimers does not appear to be applying regression coefficients to a derivative of the sample spectra to get a value used in the process control.

In contrast to the above prior art one aspect of the present invention uses an indirect measurement of monomer concentration (NIR spectra) to which correlation factors are applied based on non polymerized mixtures of solvent and monomer to predict monomer conversion under polymerization condition. The correlation factor (regression model) is developed by taking NIR calibration spectra for a series of mixtures of solvent and monomers at pressure and temperature representative of polymerization conditions. The mixtures may be generated by varying the flow rates of the monomers feed rate in the process. The composition is calculated from the mass flow rate of the monomer in the process. The calibration spectra are collected using on-line measurements in the process stream. The spectra are mathematically treated to correct for baseline variation. A number of approaches are known for doing this. A preferred approach is to apply a Savitsky-Golay odd numbered window (e.g. 5 or 7 or 9) approach to smooth out the baseline or spectra (a first or second derivative may be used). The treated spectra are then subjected to a regression analysis to convert the spectra into a linear equation similar to that suggested by Norris. The regression method can be multiple linear regression (MLR), partial least square regression (PLS) or principal component regression (PCR). The regression method generates a set of coefficient, which can be applied to new sample spectra to obtain the monomer concentration (e.g. Monomer$_b$ concentration=$b_0+b_1x_1+b_2x_2+b_3x_3+$ where $b_n$ is a regression coefficient and $x_n$ is the absorbance or derivative of the absorbance at a specific wavelength measured value).

The linear equation is verified against known samples and should have a low root mean square error of calibration (RMSEC) less than 2%, preferably significantly lower as determined by plotting calculated values (e.g. apply the same baseline correction, apply the same regression and insert the regression coefficients to provide a value) against known values (e.g. process flows etc.). The verified regression coefficients can then be directly applied to the unknown sample spectra (e.g. on line sample spectra) to determine a value (i.e. monomer(s) concentrations(s)). The value is converted to an indirect variable (e.g. monomer concentration is converted to conversion which is not measured) and the calculated conversion number is compared to a set point in the process control algorithm. None of the above art clearly expresses this subject matter.

The on-line NIR analyzer can also be utilized to verify the accuracy of process flow meters and identify process variations. For example, a calibration model can be generated using one monomer flow meter. A second flow meter can then be calibrated against the first one by comparing the predicted monomer composition versus the composition calculated form the second flow meter.

None of the above art suggest that NIR spectroscopy could be used to determine the validity of the calibration (or to recalibrate) the flow meters for a process.

U.S. Pat. No. 6,820,013 issued Nov. 16, 2004, from WO01/48458 published Jul. 5, 2001, to Frickel et al., assigned to Merk Patent GmbH, teaches a method and apparatus for the on line analysis of liquid mixtures by evaluation of binary mixtures. A library of the spectra of binary mixtures is prepared and used to evaluate the resulting mixtures. Contrary to Frickel a library or data base is not used in the present invention. Rather a series of tertiary mixtures of solvent and monomer (calibration samples) are analyzed and fitted to a linear function to provided correlation factors. These correlation factors are then applied directly to the sample spectra or portions of the sample spectra to indirectly determine a derivative value (conversion).

An additional advantage of the present invention is that the calculated correlation/regression factors are transferable among sites using the same or comparable processes. (e.g. solution to solution processes). So that the correlation factors may be calculated in a pilot scale facility but applied in commercial scale facility.

ASTM method E 1655-00 Standard Practices for Infrared Multivariate Quantative Analysis specifies at section 17.1.1 that the calibration samples must contain all chemical components which are expected to be present in the samples which are to be analyzed. Contrary to the approach of the ASTM the present invention successfully implements the use of calibration samples which do not contain all of the elements (i.e. polymer) in the calibration samples.

The present invention seeks to provide a method for process control in situations where direct measurement of a calibration value is difficult or not possible without the use of a library of spectra. Derivatives of the calibration spectra are used to generate a series of regression coefficients which are applied to a sample spectra to determine a direct value which is used to further determine an indirect or derivative value (conversion). The derivative value is compared to a set point for the process control and the process conditions are varied accordingly. This is a simple double derivative NIR process control process. Only solvent monomer mixtures are used to derive the regression coefficients factors applied to a NIR process sample to infer a secondary value which is used to modify a further secondary parameter to control the process.

The above process may also be used to verify the calibration of flow meters on line.

Additionally the process may also be used to determine the monomer concentration in the feed up stream of the reactors.

SUMMARY OF THE INVENTION

The present invention provides an on-line real time process to control the polymerization of one or more alpha olefin monomers having from 2 to 8 carbon atoms in a process from which samples of the reaction mixture can not be obtained comprising:

i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;

ii) pre-processing all or a portion of said calibration NIR spectra to eliminate baseline shift;

iii) regressing the said pre-processed calibration NIR spectra to the monomer(s) concentration as determined by mass balance, using the mass flow of each component going through the polymerization process, in absence of reaction, over wavelengths at which the absorbance of the polymer product does not significantly impact the absorbance of the monomer(s) to obtain the regression coefficients for each monomer of interest;

iv) validating the regression coefficients by collecting sample spectra, in the presence of polymer in the absence of polymer, or both, and subjecting the sample spectra to the same pre-processing of step ii) and applying the regression coefficients to the sample spectra at which the absorbance of the polymer product does not significantly impact the absorbance of the monomer(s) of interest and plotting the calculated value of the monomer of interest against the known concentration and determining the root mean square error of the predicted value;

v) if the root mean square error of the predicted concentration of the monomer of interest is greater than 1% repeating steps ii), iii) and iv) until the root mean square error of the predicted concentration of the one or more monomers of interest is less than 1%;

vi) during polymer production continuously or periodically obtaining NIR sample spectra of at one or more locations in the process;

vii) pre-processing the said polymerization NIR sample spectra to eliminate baseline shift and applying the regression coefficients determined in step v) over wavelengths at which the absorbance of the polymer product does not significantly impact the absorbance of the monomer(s) of interest to determine the concentration of one or more monomer(s) of interests at said one or more locations;

viii) calculating the monomer conversion (or degree of reaction) using a method selected from the group consisting of monomer mass flow and the measured monomer concentration in the feed at said one or more locations;

ix) comparing the value obtained from step viii) to the conversion set point in the process control algorithms; and x) as required, adjusting catalyst flow to the reactor to achieve the desired conversion.

The present invention also provides the above process, wherein the NIR spectra are obtained using a spectrophotometer having a resolution of not less 5 nm over the region in which the spectra is taken.

The present invention also provides the above process, wherein the spectra are digitized.

The present invention also provides the above process, wherein the calibration and sample NIR spectra are preprocessed to eliminate baseline shift by calculating the first or second derivative of the spectra using the Savitsky-Golay model using a window having an odd number of points.

The present invention also provides the above process, wherein a microprocessor is used to calculate said first or second derivative of the spectra.

The present invention also provides the above process, wherein in the regression of the preprocessed spectra is calculated using a method selected from the group consisting of a multiple least squares or partial least squares regression.

The present invention also provides the above process, wherein the regression is calculated using a microprocessor.

The present invention also provides the above process, wherein a microprocessor is used to calculate the comonomer concentration from the preprocessed sample spectra by applying the regression coefficients for said monomers.

The present invention also provides the above process, wherein a microprocessor is used to calculate the monomer(s) conversion and compare the calculated conversion value to the conversion set point in the process control algorithm.

The present invention also provides the above process, wherein a microprocessor is used to adjust the catalyst flow.

The present invention also provides the above process, which is continuous.

The present invention also provides the above process, wherein the root mean square error of the predicted concentration of the monomer of interest is less than 1%.

The present invention also provides the above process, wherein the monomers of interest are selected from the group consisting of ethylene, butene, hexene and octene.

The present invention also provides the above process, wherein at least one probe is down stream of a reaction zone.

The present invention also provides the above process, wherein the wavelengths at which the absorbance of the polymer product does not significantly impact the absorbance of the monomer(s) is from 1550 to 1680 nm.

The present invention also provides the above process, wherein range of temperature, pressures and monomer concentration representative of a broad envelope of polymerization includes a temperature from 125° C. to 250° C. typically from 125° C. to 230° C., and a pressure from $2.4 \times 10^3$ kPa (350 psi) to $3.1 \times 10^4$ kPa (4500 psi).

The present invention also provides the above process, which is a solution polymerization process and the monomers of interest are selected from the group consisting of ethylene, butene and octene.

The present invention also provides the above process, wherein in the calibration spectra are taken at a weight % of total stream composition in ranges from 0 to 3 wt % for ethylene and 0 to 30 wt % for octene.

The present invention also provides an on-line real time process to verify calibration on monomer flow meters in the polymerization of one or more alpha olefin monomers having from 2 to 8 carbon atoms in a process from which samples of the reaction mixture can not be obtained comprising:

i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;

ii) pre-processing all or a portion of said calibration NIR spectra to eliminate baseline shift;

iii) regressing the said pre-processed calibration NIR spectra to the monomer(s) concentration as determined by mass balance, using the mass flow of each component going through the polymerization process, in absence of reaction, over wavelengths at which the absorbance of the polymer product does not significantly impact the absorbance of the monomer(s) to obtain the regression coefficients for each monomer of interest;

iv) validating the regression coefficients by collecting sample spectra, in the presence of polymer, in the absence of polymer or both, presence of polymer and subjecting the sample spectra to the same preprocessing of step ii) and applying the regression coefficients to the sample spectra at which the absorbance of the polymer product does not significantly impact the absorbance of the monomer(s) of interest and plotting the calculated value of the monomer of interest against the known concentration and determining the root mean square error of the predicted value;

v) if the root mean square error of the predicted concentration of the monomer of interest is greater than 1% repeating steps ii), iii) and iv) until the root mean square error of the predicted concentration of the one or more monomers of interest is less than 1%;

vi) during polymer production continuously or periodically obtaining NIR sample spectra of at one or more locations in the process;

vii) pre-processing the said polymerization NIR sample spectra to eliminate baseline shift and applying the regression coefficients determined in step v) over wavelengths at which the absorbance of the polymer product does not significantly impact the absorbance of the monomer(s) of interest to determine the concentration of one or more monomer(s) of interests at said one or more locations;

viii) calculating the monomer concentration at the location of the probe using the process control algorithm and the mass flow of the monomer(s) and solvent;

ix) comparing the calculated value obtained from step viii) to the measured concentration of one or more monomers of interest at said one or more locations and determining any error in the flow meters for said one or more monomers.

The present invention also provides each of the further embodiments described in relation to the indirect control or a reaction relative to the process for on-line real time process to verify calibration on monomer flow meters in the polymerization of one or more alpha olefin monomers having from 2 to 8 carbon atoms.

The above process may also be applied to determine the monomer concentration in a feed stream up stream of a reactor. There is no polymer present in the stream while not necessary, preferably the spectra are taken at the same wavelengths as those for when the monomer is present.

Thus in a further embodiment the present invention provides an on-line real time process to determine the concentrations of one or more alpha olefin monomers having from 2 to 8 carbon atoms in a feed stream up stream from a reactor from which samples of the reaction mixture can not be obtained comprising:

i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;

ii) pre-processing all or a portion of said calibration NIR spectra to eliminate baseline shift;

iii) regressing the said pre-processed calibration NIR spectra to the monomer(s) concentration as determined by mass balance, using the mass flow of each component going into the feed stream, optionally over wavelengths at which the absorbance of the polymer product does not significantly impact the absorbance of the monomer(s) to obtain the regression coefficients for each monomer of interest;

iv) validating the regression coefficients by collecting additional sample spectra, subjecting the sample spectra to the same preprocessing of step ii) and applying the regression coefficients to the sample spectra optionally at which the absorbance of the polymer product does not significantly impact the absorbance of the monomer(s) of interest, and plotting the calculated value of the monomer of interest against the known concentration and determining the root mean square error of the predicted value;

v) if the root mean square error of the predicted concentration of the monomer of interest is greater than 1% repeating steps ii), iii) and iv) until the root mean square error of the predicted concentration of the one or more monomers of interest is less than 1%.

The concentration of monomer in the feed stream prior to the reactor (e.g. as determined above) may be directly compared to the concentration of monomer in the reactor or exiting the reactor to calculate the conversion (e.g. the second procedure in step (viii).

The present invention also provides a method to calculate a validated regression coefficient transferable between the same processes (e.g. solvent polymerization to solvent polymerization) comprising:

i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;

ii) pre-processing all or a portion of said calibration NIR spectra to eliminate baseline shift;

iii) regressing the said pre-processed calibration NIR spectra to the monomer(s) concentration as determined by mass balance, using the mass flow of each component going into the feed stream, preferably over wavelengths at which the absorbance of the polymer product does not significantly impact the absorbance of the monomer(s) to obtain the regression coefficients for each monomer of interest;

iv) validating the regression coefficients by collecting additional sample spectra, subjecting the sample spectra to the same preprocessing of step ii) and applying the regression coefficients to the sample spectra [at which the absorbance of the polymer product does not significantly impact the absorbance of the monomer(s) of interest] and plotting the calculated value of the monomer of interest against the known concentration and determining the root mean square error of the predicted value;

v) if the root mean square error of the predicted concentration of the monomer of interest is greater than 1% repeating steps ii), iii) and iv) until the root mean square error of the predicted concentration of the one or more monomers of interest is less than 1%.

DETAILED DESCRIPTION

The near infrared (NIR) spectrum covers the wavelengths from 800 nanometers (nm) to about 2500 nm. This wavelength is just above the wavelengths of visible light. NIR spectroscopy has both advantages and disadvantages. The NIR light transmits well over fiber optics permitting the probe to be up about 150 meters distant from the detector and/or light source (typically a light source and a grating to split the light into different wave lengths). One disadvantage is that there may be a number of overlapping adsorption bands which may make it difficult to interpret a spectrum. For solutions of polymer and monomers in an aliphatic solvent there are areas where the absorption spectra overlap and make it difficult to interpret the results. For example the C—H stretching will be generated by monomers, solvent and polymer. (i.e. the first and second C—H stretching overtones—about 1650-1700 nm and 1100-1250 nm). However for the C=C stretch in the region from about 1500 to 1700 nm, preferably from 1550 to 1680, on the edge of the first C—H stretching overtone the polymer and solvent should provide only a minimal amount of interference. Accordingly it is possible to select a region of the NIR spectra where the monomer absorption is relatively free of interference from the polymer product and the solvent.

The same might be said of slurry polymerization relative to the diluents, monomers and polymer and also of gas phase reactions, and particularly condensing modes relative to the condensing component, the monomers and polymer.

Given the narrow range of wavelength over which there is a minimum interference of monomer and product and solvent, etc. the spectrophotometer (e.g. detector) should have a resolution of better than 5 nm, preferably more than about 3 nm, most preferably better than about 2 nm.

In the practice of the present invention as the spectra are mathematically treated generally the spectra (both calibration and sample) are obtained in digital form or digitized.

For a process such as medium to high pressure solution polymerization of one or more alpha olefins having from 2 to 8 carbon atoms it is not possible to acquire samples directly from the reaction system and therefore it has not been possible to prepare calibration spectra or derivatives thereof. In the present invention this problem is overcome by generating a series of samples of monomers in the solvent at pressure and temperature representative of polymerization conditions in situ, in a pilot plant facility and building a calibration model using wavelength that will not be significantly impacted by the presence of polymer.

Alternatively, this could be done by making appropriate mixtures of solvent and one or more, preferably multiple monomers (as outlined below) including polymer, in a laboratory environment and taking the NIR spectrum over the desired wavelength (e.g. that suggested above). However, such samples cannot be easily prepared in a laboratory environment due to the high pressure and temperature required to dissolve the polymer and produce conditions that are similar to reaction conditions.

A preferred method to prepare calibration spectra is to run the reaction system, without catalyst, and hence no polymer, at different temperatures (a broad envelop of process conditions) so that temperature is implicitly included in the calibration curve. The spectra of different tertiary mixtures of solvent and monomers may be taken with one or more probes installed at various locations such as in the reactor or reactors if there are multiple reactors (in series or parallel) or at inlets or outlet to the reactors, or other reasonable locations. Although it is possible to take the calibration and sample spectra at multiple points it may not be necessary if the calibration is representative of a broad range of process conditions. One advantage of this method of generating calibration spectra is that samples are generated typically under operating conditions in the absence of reaction so they do not need to be corrected for temperature or pressure.

Typical operating conditions for solution polymerization of alpha olefins may range from a temperature from 125° C. to 250° C., typically from 125° C. to 230° C. and a pressure from $2.4 \times 10^3$ kPa (350 psi) to $3.1 \times 10^4$ kPa (4500 psi), preferably from 160° C. to 230° C. and a pressure from $2.75 \times 10^3$ kPa (400 psi) to $2.75 \times 10^4$ kPa (4000 psi).

The calibration samples typically comprise a mixture of solvent and the monomers to be polymerized. In some instances it may be useful to obtain a sample of pure monomer in solvent. For solution polymerization the calibration samples may be generated over a fairly narrow range of monomer concentrations. For example for the ethylene component the weight % of ethylene in the calibration sample may range from about 0 to 10 weight % preferably from 0 to about 8 weight %, more preferable from 0 to about 5 weight %, desirably from 0 to 3 weight % (based on the composition). For the comonomer (e.g. 1-octene), calibration sample the weight % of comonomer may range from about 0 to 30 weight % preferably from 0 to about 20 weight %, more preferably from 0 to about 15 weight % (based on the weight of the composition). When operating in the above manner the amount of monomer and solvent in the calibration sample/spectra is calculated based on the flow meters for the monomers and solvent into the reaction system.

For the embodiment where the process is used to verify the calibration of the flow meters the NIR calibration model provides a baseline against which the flow meters may be verified.

Such a method comprises:

i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;

ii) pre-processing all or a portion of said calibration NIR spectra to eliminate baseline shift;

iii) regressing the said pre-processed calibration NIR spectra to the monomer(s) concentration as determined by mass balance, using the mass flow of each component going through the polymerization process, in absence of reaction, optionally over wavelengths at which the absorbance of the polymer product does not significantly impact the absorbance of the monomer(s) to obtain the regression coefficients for each monomer of interest;

iv) validating the regression coefficients by collecting sample spectra, in the presence of polymer, in the absence of polymer, or both, and subjecting the sample spectra to the same pre-processing of step ii) and applying the regression coefficients to the sample spectra at which the absorbance of the polymer product does not significantly impact the absorbance of the monomer(s) of interest and plotting the calculated value of the monomer of interest against the known concentration and determining the root mean square error of the predicted value;

v) if the root mean square error of the predicted concentration of the monomer of interest is greater than 1% repeating steps ii), iii) and iv) until the root mean square error of the predicted concentration of the one or more monomers of interest is less than 1%;

vi) during polymer production continuously or periodically obtaining NIR sample spectra of at one or more locations in the process;

vii) pre-processing the said polymerization NIR sample spectra to eliminate baseline shift and applying the regression coefficients determined in step v) over wavelengths at which the absorbance of the polymer product does not significantly impact the absorbance of the monomer(s) of interest to determine the concentration of one or more monomer(s) of interests at said one or more locations;

viii) calculating the monomer concentration at the location of the probe using the process control algorithm and the mass flow of the monomer(s) and solvent;

ix) comparing the calculated value obtained from step viii) to the measured concentration of one or more monomers of interest at said one or more locations and determining any error in the flow meters for said one or more monomers.

Preferred monomers for solution polymerization are ethylene and one or more of butene and octene, preferably octene.

The resulting calibration spectra for each reactor or location (although as noted above provided the process conditions for the calibration samples are broad enough you may only need one location) are then treated mathematically to correct for baseline variations of the spectra or to smooth out the spectra. Many methods of mathematical treatment to correct for baseline error and or smoothing are known to those skilled in the art (i.e. a derivative calculation over a moving range). One useful method is to process the spectra using the Savitsky-Golay method using a window having an odd number of points (e.g. a window of 9 points, 7 points or 5 points could be used.). The first or second derivative may be used in the process of the present invention. The calibration spectra might also be treated with multiplicative scatter correction, and even one or more digital filters The corrected calibration spectra are then correlated to the concentration of monomer using a multi linear regression process (e.g. multiple least squares (MLS) or partial least squares fit (e.g. PLS1 or PLS2), principle component regression (PCR), neural networks etc. or combinations thereof). This generates a series of regression coefficients for the fit or each spectra or component of each spectra to monomer concentration (e.g. concentration of monomer $y=b_0+x_1Xb_1+x_2Xb_2+$ etc. where $b_n$ is a regression coefficient and $x_n$ is a measured value—the absorbance or derivative thereof, at wavelength n.

The regression coefficients then need to be validated. That is a series of spectra of samples containing known amounts of the different monomers are subjected to the same baseline correction/curve smoothing as the calibration spectra. Then the regression coefficients are applied to the values derived from the spectra. Then a plot of the calculated values against the known values is made. This plot should be linear or substantially linear. From the linear plot it is possible to determine a number of factors including: the slope, the intercept, the offset, the Root Mean Square Error of the Prediction (RMSEP); the bias of the prediction, the correlation, and the Standard Error of Calibration (SEC). Provided the RMSEP is sufficiently low the regression coefficients may be used to calculate values for monomer concentration. The RMSEP should be less than 5, preferably less than 1, most preferably less than 0.5 desirably less than 0.3 weight % of the measured monomer concentration. The validation plot of calculated values to know values should have a correlation to the actual values of greater than 98%, preferably greater than 99%, most preferably greater than 99.5%.

Once the regression coefficients have been validated the model may be used to determine the on-line concentration of monomer(s). Sample or operating spectra taken at one or more on-line locations, preferably the same as for the calibration spectra are taken over the same wavelength or wavelengths as for the calibration spectra. The resulting spectra is then subjected to the same mathematical treatment to correct for baseline variations of the spectra or to smooth out the spectra. Many methods of mathematical treatment to correct for baseline error and or smoothing are known to those skilled in the art (i.e. a derivative calculation over a moving range). One useful method is to process the spectra using the Savitsky-Golay model using a window having an odd number of points (e.g. a window of 9 points, 7 points or 5 points could be used.)

The regression coefficients are then applied directly to the derivative spectra to predict the concentration of the monomers.

The validated regression coefficients calculated in accordance with the present invention may be transferred among/between plants using the same process. For example a validated regression coefficient generated at a solution polymerization pilot plant may be transferred to a commercial scale solution polymerization plant using comparable technology (NOVA Chemicals Advanced SCLAIRTECH Technology pilot plant to a commercial Advanced SCLAIRTECH Technology plant). Additionally, validated regression coefficients generated at a commercial solution polymerization plant could be transferred to another comparable plant (from the licensor's process to a licensee's process)

In one embodiment of the invention the monomer concentration is then converted to a conversion. In a simplest approach the operator knows how much of each monomer has been fed to the reactor. If the measurement is taken at the outlet of the reactor the operator knows the concentration of monomers in the stream leaving the reactor. It is a simple matter to calculate the conversion of monomer to polymer. The calculated conversion may then be compared to the set point value for the conversion. As a result of this comparison for example the rate of addition of catalyst may be or is controlled to obtain the desired conversion. One can envision other process control procedures. For example in short residence time reactors (under 5 minutes) the direct control of catalyst may be the best way to control the conversion. In longer residence time reactors (greater than 5 minutes, typically greater than 15 minutes, preferably greater than 30 minutes) one or more of catalyst concentration, monomer(s) concentration, reaction temperature, catalyst activity (e.g. add a controlled amount of catalyst poison) and possibly chain transfer agent (e.g. $H_2$) could be used to control the conversion The process of the invention could be further automated. For example the baseline correction or curve smoothing algorithms or process could be programmed into a computer or a microprocessor together with the regression coefficients. Additionally the output from the sample spectra could be fed to the computer or microprocessor. The computer or microprocessor would then calculate the monomer concentration. The monomer concentration can then be passed on to the Distributed Control System (DCS) using a communication protocol, such as ModBus. The DCS can perform further calculations, (e.g. conversion) and then can be used to control the process so the operation would be essentially automatic once the regression coefficients have been calculated. While this aspect of the present invention refers to a computer or microprocessor the present invention could be implemented using a number of computers or a neural network or Distributed Control System (DCS) to control the process.

The present invention will now be illustrated by the following non limiting examples.

EXAMPLES

Standardizing or Referencing the NIR Probe and Associated Fiber Optic Links

Manufactures of NIR probes and spectroscopes suggest "referencing" the equipment prior to use. Typically they suggest "referencing" in the presence of an inert gas. The referencing provides a baseline for all subsequent measurements. For the present application it was decided to reference the NIR and probe against solvent for the reaction. This was done because as a practical matter one does not want to shut down and empty a reactor to do a baseline check.

Calibration

Typically data for NIR calibration curves are generated in a laboratory setting. However, for the present example a Guided Wave® custom single sided probe having a 15 mm path length was inserted into a process "T" in NOVA Chemicals solution pilot plant at the outlet to the second reactor (item 18 in FIG. 1), just downstream from the deactivator injection point (16). The probe was connected to a Guided Wave® InSite IV laboratory spectrophotometer having a wavelength range from 1000 to 2100 nanometers.

Figure 1:
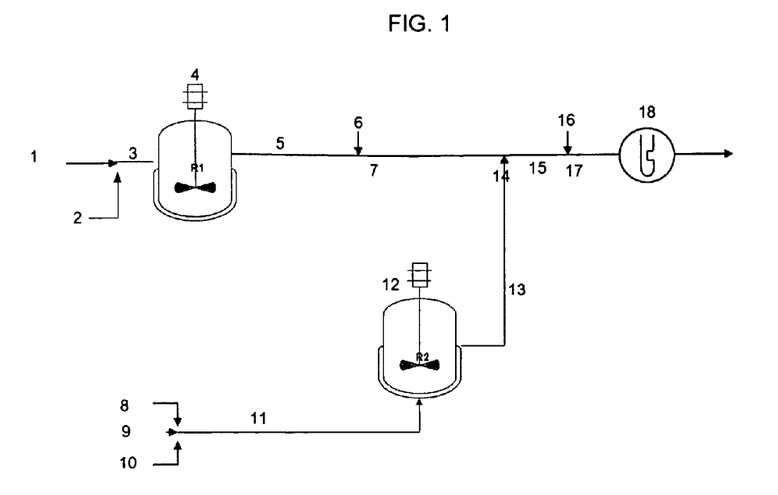
FIG. 1 is a schematic drawing of the reactor configuration to provide calibration and validation curves for a method of the present invention.

FIG. 1 is a schematic representation of NOVA Chemicals pilot plant. The schematic shows the reactor configuration utilized to develop and validate the NIR calibration. Solvent (1) and 1-octene (2) flow through line 3 to a first continuously stirred reactor (4). Solvent (8), 1-octene (9) and ethylene (10) flow through line 11 to a second continuously stirred tank reactor (12). The output of the first reactor (4) is line 5. Deactivator (6) flows into line 5 at 7 up stream of the junction 14 of the output 13 of the second reactor (12) with line 7. Downstream of junction 14 additional ethylene monomer feed (16) may be fed to line 15 at 17 up stream of near infrared sensor (18). In FIG. 1 the reactors are shown in parallel mode.

Spectra for solutions of ethylene and 1-octene at 190° C. were obtained. The baseline corrected samples showed strong peaks C=C absorbance peaks in the first 1600-1660 nm and second 1100-1250 overtones. The first overtone was selected as the appropriate region of the spectra for the experiments.

Using a central cubic experimental design mixtures of ethylene, octene and solvent were run through the pilot plant absent a catalyst and any reaction (i.e. no polymer was present in the calibration spectra). The amounts of ethylene and 1-octene in the samples was calculated from the flow meters and any required offset.

Figure 2:
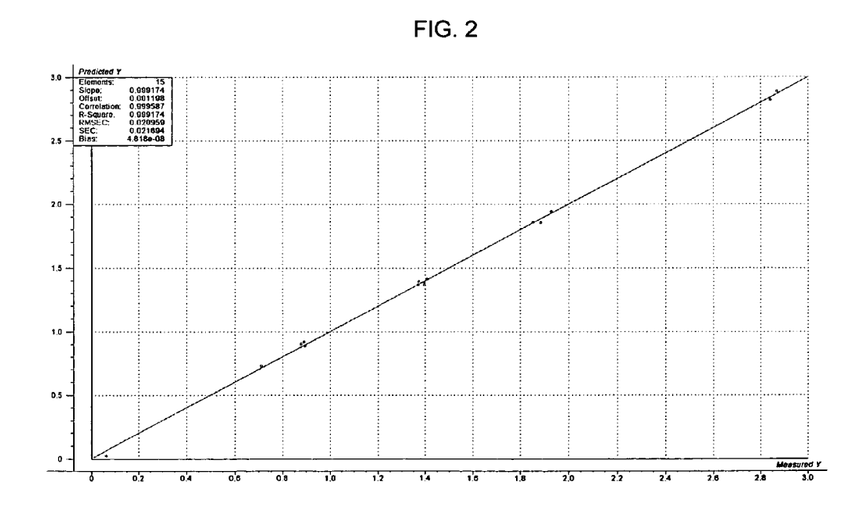
FIG. 2 is a verification plot for calculated values for ethylene using the method of the present invention against known samples.

The resulting spectra (digitized) were preprocessed using a computer using the Savitsky-Golay method (with a window of 9 points. Note later the window was changed to 5 points) to provide a second derivative of the digitized spectra (or spectra data). Subsequently, it was confirmed that the first derivative is equally useful in the process of the present invention. The digitized derivatives of the spectra (or relevant portions of the spectra) were then subject to a partial least squares regression to generate regression coefficients for monomer concentration (wt % in solvent). The predicted monomer concentration is compared with the reference method in (FIG. 2). The root mean square error for the regression coefficients for the calibration were 0.02% for ethylene and 0.22% for 1-octene.

Validation

Figure 3:
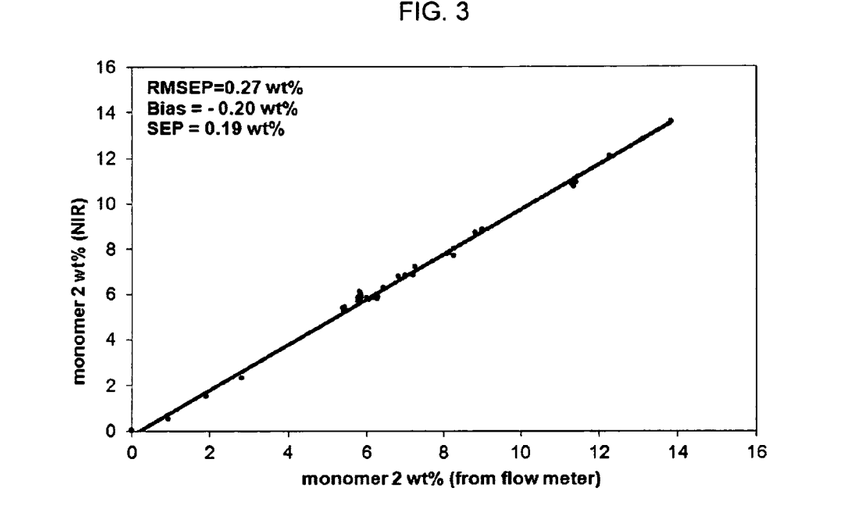
FIG. 3 is a verification plot of the calculated values for 1-octene using the method of the present invention. The data was generated by adding known amount of 1-octene post-reactor upstream of the NIR probe using the reactor configuration shown in FIG. 1. Reactor 2 (item (12) in FIG. 1) was producing homopolymer.
Figure 4:
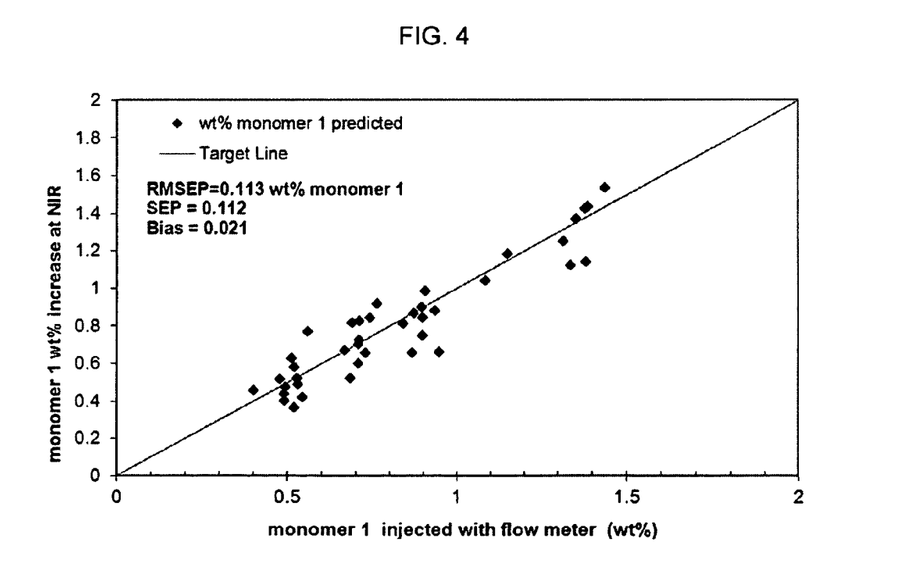
FIG. 4 is a verification plot for calculated values for ethylene using the method of the present invention against known samples. The data was generated by adding known amount of ethylene post-reactor upstream of the NIR probe using the reactor configuration shown in FIG. 1.

The reactors at the pilot plant were run in parallel with the combined flow from both reactors passing the NIR detector. The first reactor (item (4) in FIG. 1) was run without catalyst and with solvent and 1-octene. The octene level ranged up to about 18 weight %. For this validation catalyst deactivator was also added after the first reactor to prevent octene reacting with the catalyst leaving the second reactor at the junction point (14). The second reactor was run in the presence of catalyst and ethylene homopolymer was prepared. The digital sample spectra were treated as above for the calibration spectra (Savitsky-Golay method (with a window of 9 points)) and the correlation factors applied to give a calculated weight % octene. This was done for a number of samples. The calculated values were plotted against the actual weight % of octene (FIG. 3). The root mean square error of the predicted value of octene relative to the actual value of octene was 0.27 wt % octene (FIG. 3). Additionally, during the validation ethylene was spiked into the outlet of the second reactor and the ethylene concentration was predicted from the spectra and compared to calculated values. This was done for a number of values of ethylene concentration (wt %) and the predicted value for ethylene was plotted against the actual value for ethylene. The root mean square error of the predicted ethylene concentration relative to the actual concentration was 0.11 wt % ethylene (FIG. 4). The "spikes" of ethylene were injected at the outlet of the second reactor upstream of the probe. The amount of ethylene ranges up to about 3 weight %. The root mean square error of the predicted ethylene concentration was not as good as the 0.02 wt % observed in the calibration step. However, the larger error is attributed to unsteady reaction during the validation step. The bias data is low (0.02 wt %) supporting that the variability is introduced by unsteady reaction (reaction rolls).

Cross Validation

The ethylene conversion for the pilot plant predicted as a result of NIR spectra using the method of the present invention were compared to calculated values based on a heat balance calculation for the reactor and a gas chromatograph analysis of the overheads in the stripper. The NIR measurement gave good results. The results were substantially the same compared to the GC analysis but the GC analysis took about 20 minutes to complete whereas the NIR results were essentially instantaneous. The GC analysis is also less responsive due to a smoothing effect in the process piping and sampling system. The results compared well with the heat balance calculations but heat balance calculation tended to have an "offset" (were lower) due to heat losses from the reactor per se.

Application

The validation and cross validation shows that the method of measuring monomer concentration and converting it to conversion is accurate. The conversion measurement may then be used to control catalyst flow to bring conversion back to a set point value for a reaction. This is preferably done using a micro-processor, including systems such as but not limited to proportional integral derivative (PID) controllers, neural nets, feedback loop control, forward control, and adaptive control and can be integrated with a Distributed Control System (DCS).

Figure 5:
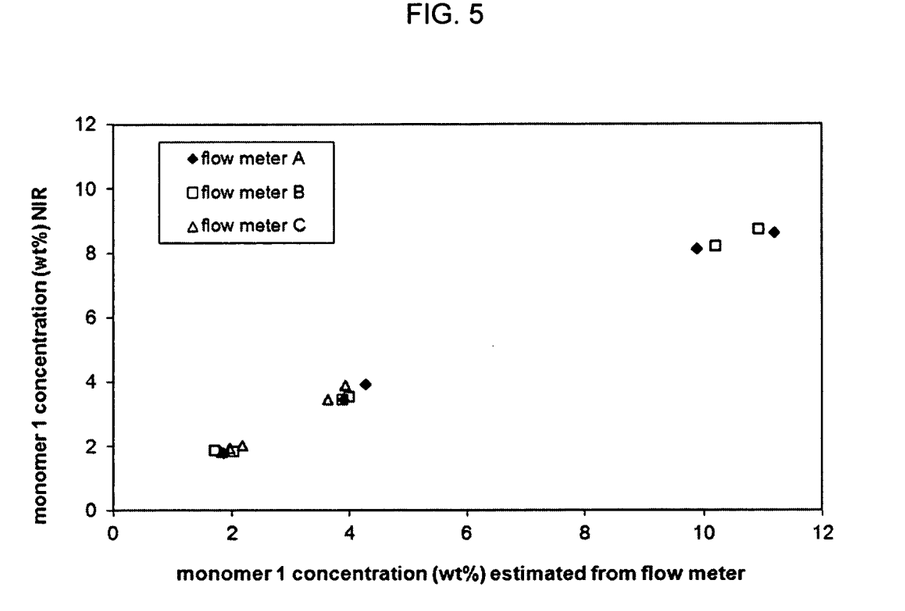
FIG. 5 is a verification plot of flow meters. It compares monomers concentration generated from different flow meters.

During the above experiments it was also determined that the concentration measurement using on-line NIR spectrometry were sufficiently precise that it is possible to utilize this technology to check the accuracy of a flow meter or compare the performance of different flow meters. The following non limiting example illustrates how the on-line NIR system can be utilize to evaluate the performance of flow meters:

The experimental set-up consist of the dual-reactor pilot plant system in FIG. 1, where the on-line NIR probe is located downstream of the second reactor. Ethylene (monomer) can be fed to the reactor using 3 different flow meters (A, B and C). The pilot plant was configured such that flow meters A, B and C were routed to go through Reactor 2 and then flow through the NIR probe. Experiments were conducted where the 3 ethylene concentrations were generated using each flow meter, in absence of reaction. The measured monomer concentration using the NIR analyzer can then be utilized to compare the performance of the flow meter and understand their relative accuracy (FIG. 5). This may be used to as an on line method to validate or recalibrate flow meters.

What is claimed is:

1. An on-line real-time process to control the polymerization of one or more alpha olefin monomers having from 2 to 8 carbon atoms in a process from which physical samples of the reaction mixture cannot be obtained comprising:
   i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;
   ii) pre-processing all or a portion of said calibration NIR spectra to eliminate baseline shift;
   iii) regressing the said pre-processed calibration NIR spectra to the monomer(s) concentration as determined by mass balance, using the mass flow of each component going through the polymerization process, in absence of reaction, over wavelengths at which the absorbance of the polymer product does not significantly impact the absorbance of the monomer(s) to obtain the independent regression coefficients for each monomer of interest;
   iv) validating the regression coefficients by collecting sample spectra, with the presence of polymer, without the presence of polymer, or both and subjecting the sample spectra to the same preprocessing of step ii) and applying the regression coefficients to the sample spectra at which the absorbance of the polymer product does not significantly impact the absorbance of the monomer(s) of interest and plotting the calculated concentration of the monomer of interest against the known concentration and determining the root mean square error of the calculated concentration of the monomer of interest;
   v) if the root mean square error of the predicted concentration of the monomer of interest is greater than 5 wt. % repeating steps ii), iii) and iv) using one or more different preprocessing methods, different regression techniques, different numbers or locations of wavelength, different pressures, temperature and concentrations of monomers of interest until the root mean square error of the predicted concentration of the one or more monomers of interest is less than 5 wt. % then;
   vi) during polymer production continuously or periodically obtaining NIR sample spectra of at one or more locations in the process;
   vii) pre-processing the said polymerization NIR sample spectra to eliminate baseline shift and applying the regression coefficients determined in step v) over wavelengths at which the absorbance of the polymer product does not significantly impact the absorbance of the monomer(s) of interest to determine the concentration of one or more monomer(s) of interests at said one or more locations;
   viii) calculating the monomer conversion (or degree of reaction) using a method selected from the group consisting of the monomer mass flow in the feed and the measured monomer concentration at said one or more locations;
   ix) comparing the value obtained from step viii) to the conversion set point in the process control algorithms; and
   x) as required, adjusting one or more of catalyst flow to the reactor monomer concentration; reaction temperature; catalyst activity and amount of chain transfer agent to achieve the desired conversion.

2. The process according to claim 1, wherein the NIR spectra are obtained using a spectrophotometer having a resolution of not less than 5 nm over the region in which the spectra is taken.

3. The process according to claim 2, wherein the spectra are digitized.

4. The process according to claim 3, wherein the calibration and sample NIR spectra are preprocessed to eliminate baseline shift by calculating the first or second derivative of the spectra using the Savitsky-Golay model using a window having an odd number of points.

5. The process according to claim 4, wherein a microprocessor is used to calculate said first or second derivative of the spectra.

6. The process according to claim 5, wherein in the regression of the preprocessed spectra is calculated using a method selected from the group consisting of a multiple least squares or partial least squares regression.

7. The process according to claim 6, wherein the regression is calculated using a microprocessor.

8. The process according to claim 7, wherein a microprocessor is used to calculate the comonomer concentration from the preprocessed sample spectra by applying the regression coefficients for said monomers.

9. The process according to claim 8, wherein a microprocessor is used to calculate the monomer(s) conversion and compare the calculated conversion value to the conversion set point in the process control algorithm.

10. The process according to claim 9, wherein a microprocessor is used to adjust the catalyst flow.

11. The process according to claim 10, which is continuous.

12. The process according to claim 11, wherein the root mean square error of the predicted concentration of the monomer of interest is less than 1 wt. %.

13. The process according to claim 12, wherein the monomers of interest are selected from the group consisting of ethylene, butene, hexene and octene.

14. The process according to claim 13, wherein at least one probe is down stream of a reaction zone.

15. The process according to claim 14, wherein the wavelengths at which the absorbance of the polymer product does not significantly impact the absorbance of the monomer(s) is from 1550 to 1680 nm.

16. The process according to claim 15 wherein range of temperature, pressures and monomer concentration representative of a broad envelope of polymerization includes a temperature from 125° C. to 250° C. and a pressure from $2.4 \times 10^3$ kPa (350 psi) to $3.1 \times 10^4$ kPa (4500 psi).

17. The process according to claim 16, which is a solution polymerization process and the monomers of interest are selected from the group consisting of ethylene, butene and octene.

18. The process according to claim 17, wherein in the calibration spectra are taken at a weight % of solvent to monomer in ranges from 0 to 3 wt for ethylene and 0 to 30 wt % for octene.

19. An on line real time process to verify the calibration of monomer flow meters for polymerization of one or more alpha olefin monomers having from 2 to 8 carbon atoms in a process from which samples of the reaction mixture cannot be obtained comprising:
   i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;
ii) pre-processing all or a portion of said calibration NIR spectra to eliminate baseline shift;
iii) regressing the said pre-processed calibration NIR spectra to the monomer(s) concentration as determined by mass balance, using the mass flow of each component going through the polymerization process, in absence of reaction, to obtain the independent regression coefficients for each monomer of interest;
iv) validating the regression coefficients by collecting sample spectra, in the presence of polymer, in the absence of polymer, or both and subjecting the sample spectra to the same preprocessing of step ii), applying the regression coefficients to the sample spectra at which the absorbance of the polymer product does not significantly impact the absorbance of the monomer(s) of interest, plotting the calculated concentration of the monomer of interest against the known concentration and determining the root mean square error of the predicted concentration;
v) if the root mean square error of the predicted concentration of the monomer of interest is greater than 5 wt. % repeating steps ii), iii) and iv) using one or more different preprocessing methods, different regression techniques, different numbers or locations of wavelength, different pressures, temperature and concentrations of monomers of interest until the root mean square error of the predicted concentration of the one or more monomers of interest is less than 5 wt. %;
vi) periodically obtaining NIR sample spectra of at one or more locations in the process in the absence of polymer;
vii) pre-processing the said NIR sample spectra to eliminate baseline shift and applying the regression coefficients determined in step v) over wavelengths of the monomer(s) of interest to determine the concentration of one or more monomer(s) of interests at said one or more locations;
viii) calculating the monomer concentration at the location of the probe using the mass flow of the monomer(s) and solvent;
ix) comparing the calculated concentration of the monomer of interest obtained from step viii) to the measured concentration of one or more monomers of interest at said one or more locations and determining any error in the flow meters for said one or more monomers.

20. An on line real time process to determine the concentrations of one or more alpha olefin monomers having from 2 to 8 carbon atoms in a feed stream, up stream from a reactor from which samples of the reaction mixture cannot be obtained comprising:
i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;
ii) pre-processing all or a portion of said calibration NIR spectra to eliminate baseline shift;
iii) regressing the said pre-processed calibration NIR spectra to the monomer(s) concentration as determined by mass balance, using the mass flow of each component going into the feed stream, over wavelengths at which the absorbance of the polymer product does not significantly impact the absorbance of the monomer(s) to obtain the independent regression coefficients for each monomer of interest;
iv) validating the regression coefficients by collecting additional sample spectra, subjecting the sample spectra to the same preprocessing of step ii) and applying the regression coefficients to the sample spectra at which the absorbance of the polymer product does not significantly impact the absorbance of the monomer(s) of interest and plotting the calculated concentration of the monomer of interest against the known concentration and determining the root mean square error of the predicted concentration of the monomer of interest;
v) if the root mean square error of the predicted concentration of the monomer of interest is greater than 1 wt. % repeating steps ii), iii) and iv) using one or more different preprocessing methods, different regression techniques, different numbers or locations of wavelength, different pressures, temperature and concentrations of monomers of interest until the root mean square error of the predicted concentration of the one or more monomers of interest is less than 1 wt. %.

21. A method to calculate and validate independent regression coefficients for one or more alpha olefin monomers having from 2 to 8 carbon atoms of interest transferable between plants using the same processes comprising:
i) collecting on-line NIR calibration spectra of sample mixtures of solvent and monomers in a polymerization process, in the absence of reaction, at one or more locations in the polymerization process, over a range of temperature, pressures and monomer concentration representative of a broad envelope of polymerization conditions to generate a set of calibration NIR spectra;
ii) pre-processing all or a portion of said calibration NIR spectra to eliminate baseline shift;
iii) regressing the said pre-processed calibration NIR spectra to the monomer(s) concentration as determined by mass balance, using the mass flow of each component going into the feed stream, over wavelengths at which the absorbance of the polymer product does not significantly impact the absorbance of the monomer(s) to obtain the independent regression coefficients for each monomer of interest;
iv) validating the regression coefficients by collecting additional sample spectra, subjecting the sample spectra to the same preprocessing of step ii) and applying the regression coefficients to the sample spectra at which the absorbance of the polymer product does not significantly impact the absorbance of the monomer(s) of interest and plotting the calculated concentration of the monomer of interest against the known concentration and determining the root mean square error of the predicted value;
v) if the root mean square error of the predicted concentration of the monomer of interest is greater than 1 wt. % repeating steps ii), iii) and iv) using one or more different preprocessing methods, different regression techniques, different numbers or locations of wavelength, different pressures, temperature and concentrations of monomers of interest until the root mean square error of the predicted concentration of the one or more monomers of interest is less than 1 wt. %.

* * * * *